(12) United States Patent
Beck et al.

(10) Patent No.: US 7,573,365 B2
(45) Date of Patent: Aug. 11, 2009

(54) HUMIDITY SENSOR

(75) Inventors: David B. Beck, West Jordan, UT (US);
John A. Sindt, Sandy, UT (US);
Thomas E. Danielson, Sandy, UT (US)

(73) Assignee: Sensitron, Inc., Draper, UT (US)

( * ) Notice: Subject to any disclaimer, the term of this patent is extended or adjusted under 35 U.S.C. 154(b) by 306 days.

(21) Appl. No.: 11/301,057

(22) Filed: Dec. 12, 2005

(65) Prior Publication Data

US 2007/0132542 A1   Jun. 14, 2007

(51) Int. Cl.
*H01C 7/00* (2006.01)
(52) U.S. Cl. ...................................................... 338/35
(58) Field of Classification Search .................... 338/35
See application file for complete search history.

(56) References Cited

U.S. PATENT DOCUMENTS

| | | | |
|---|---|---|---|
| 5,005,107 A * | 4/1991 | Kobashi et al. | 361/540 |
| 5,157,372 A | 10/1992 | Langford | |
| 5,583,476 A | 12/1996 | Langford | |
| 6,724,201 B2 | 4/2004 | Sato et al. | |
| 6,812,821 B2 * | 11/2004 | Fujita et al. | 338/34 |
| 6,883,371 B2 * | 4/2005 | Sugaya et al. | 73/335.05 |

OTHER PUBLICATIONS

International Search Report, mailed Jul. 25, 2007.
Written Opinion of the International Searching Authority, mailed Jul. 25, 2007.
PCT, International Search Report, date of mailing—Oct. 1, 2008.
PCT, Written Opinion of the International Searching Authority, date of mailing—Oct. 1, 2008.
Patent Cooperation Treaty, International Preliminary Report on Patentability, date of mailing Mar. 2, 2009.

* cited by examiner

*Primary Examiner*—Elvin G Enad
*Assistant Examiner*—Joselito Baisa
(74) *Attorney, Agent, or Firm*—Holme Roberts & Owen, LLC

(57) ABSTRACT

A system and method for a resistor for detecting the relative level of moisture content in a humid environment. The resistor has a first layer of conductive material on a top surface of a substrate having a bend. The conductive material is exposed to atmospheric conditions. The first layer of conductive material has a static condition moisture content and a measurable electrical resistance that changes predictably when the amount of moisture content in contact with the first layer of conductive material changes from the static condition. The change of resistance of the first layer of conductive material corresponds to a change in the moisture content in contact with the first layer of electrically conductive material.

31 Claims, 6 Drawing Sheets

HUMIDITY SENSOR

BACKGROUND OF THE INVENTION

1. The Field of the Invention

This invention relates to electrical components and more particularly to sensors for detecting humidity and even more particularly to sensors which predictably vary in electrical resistance with variations in humidity.

2. The Relevant Technology

Humidity is often viewed as a measure of the water content in air. High humidity (e.g., 70% relative humidity) generally means that more water vapor is present in the air in relation to air with less water vapor in it. Of course, humidity may also be the measure of any other liquid vapor in any other gas. Sensors to measure humidity are known and can range from a material that changes color in relation to changes in humidity to mechanical devices that move in relationship to amount of liquid vapor in the gas. While flexible potentiometers U.S. Pat. No. 5,157,372 (Langford) and U.S. Pat. No. 5,583,476 (Langford), (which are incorporated herein for all purposes), have been sold commercially for measuring the amount of movement from a first configuration to a second configuration, no flexible potentiometer is currently known configured or adapted to measure the amount of liquid (e.g., water) vapor in a gas such as the air or atmosphere in contact with the surface of the flexible potentiometer.

BRIEF SUMMARY OF THE INVENTION

In various exemplary embodiments of the present invention, a deflectable resistor is provided that is put in a permanent fixed bent configuration. In general, the deflectable resistor comprises a substrate and a first layer of conductive material. The substrate is formed of a deflectable or bendable electrical insulating material having a top surface, a first end, a second end, a width and a length between the first end and the second end. The substrate is configured to have at least one bend having a pre-selected curvature, radius or radii between the first end and the second end.

A first layer of conductive material has a first end oriented toward proximate the first end of the substrate a second end oriented toward the second end of the substrate. The first layer also has a width and a length that extends between the first end and the second end is disposed on a surface of the substrate and over the bend thereby widening cracks and opening more cracks in the first layer. The first layer of conductive material has an electrical resistance measured between the first end and said second end that changes predictably with the change in humidity of a gas proximate the first layer.

In operation, the gas proximate the first layer of conductive material has or includes a liquid vapor, the humidity being an indication of the amount of liquid vapor in the gas. In operation, it is believed that the molecules of the liquid vapor in the gas migrate into the cracks in the first layer. Molecules of the liquid vapor in the cracks change the electrical conductivity and in turn the resistance of the first layer. Upon application of an electrical potential across the first layer, the change in humidity will cause a predictable change in the resistance and in turn in the electric current or voltage all of which can be calculated and presented to a user in a visual form that reflects or indicates the amount of liquid vapor or humidity.

In another preferred arrangement, a layer of electrically conductive ink is deposited on a surface of the substrate. In a preferred configuration, the length and said width of the layer of electrically conductive ink is less than the length and said width of the substrate. The layer of conductive ink has a resistance measured between the first end and the second end of the layer of electrically conductive ink that changes predictably with a change in the liquid vapor in the gas.

In an alternate arrangement, the deflectable resistor further comprises a first connector means coupled to the first layer of electrically conductive ink for interconnection to external electrical components and a second connector means coupled to the layer of conductive material for interconnection to external electrical components.

In a more preferred configuration, the substrate has at least one manufactured bend of a preselected radius or radii for use in a high humidity environment.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DESCRIPTION OF A PREFERRED EMBODIMENT

Figure 1:
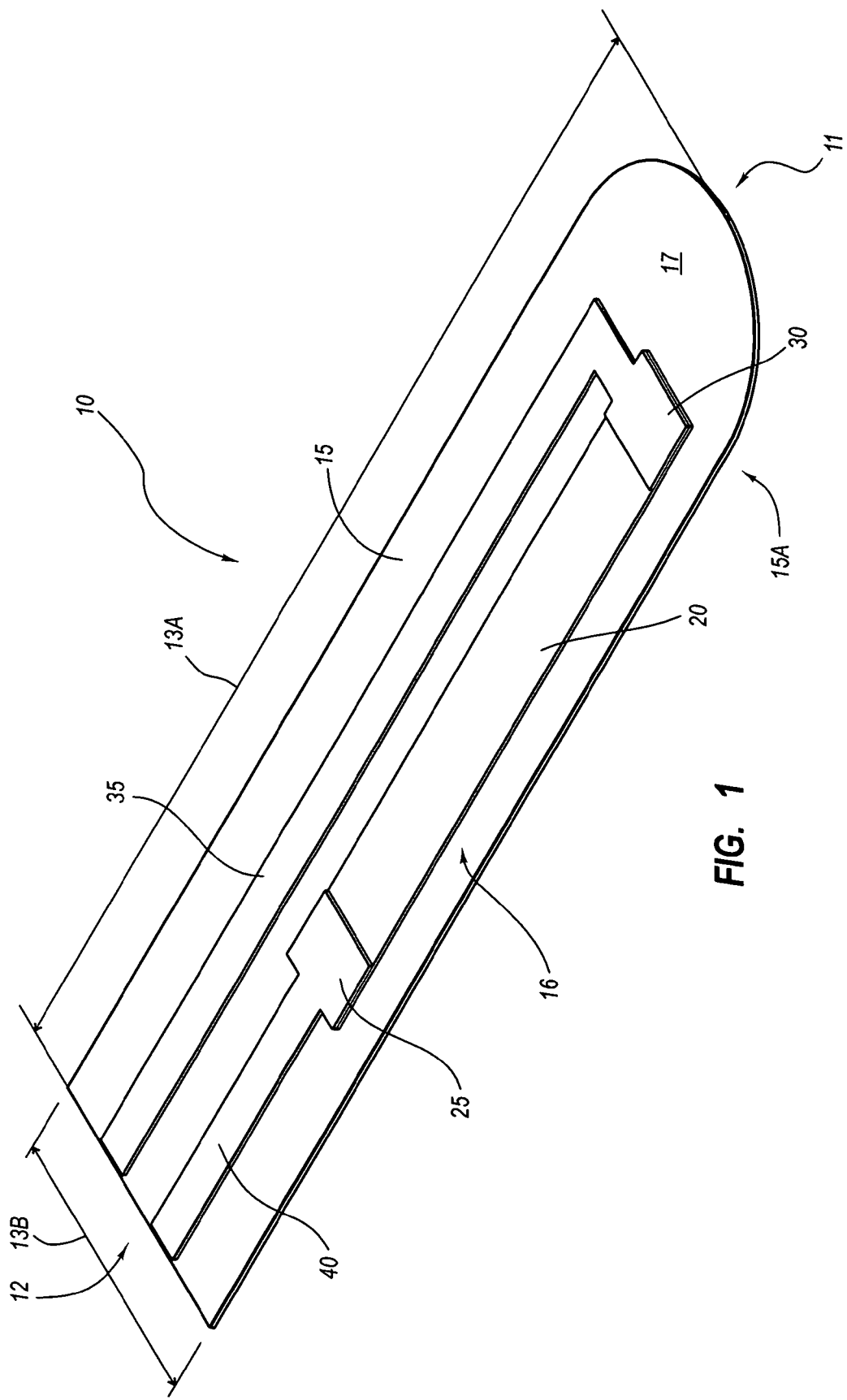
FIG. 1 illustrates a top perspective view of a humidity sensitive sensor in accordance with the present invention.

FIG. 1 illustrates a top perspective view of a humidity sensitive sensor 10. Humidity sensitive sensor 10 generally comprises a substrate 15 having both a top surface 17 and a bottom surface 15A and a layer of conductive material 16 disposed on one of the surfaces. The substrate 15 has a first end 11, a second end 12, a length 13A that extends between the first end 11 and the second end 12 and a width 13B. In the illustrated embodiment, the layer of variable resistance or conductive material 16 is disposed on the top surface 17 of the substrate 15 of the humidity sensitive sensor 10.

Substrate 15 is formed of an insulating material. Various types of phenolic resin materials are presently believed to be suitable as the substrate. The substrate may also be constructed of various materials including various polymers, such as polyamide, polyimide (Kapton), and polyester (Mylar), which may be thermoplastics. While the above substrates are deflectable, they need not be configured to be flexible or to experience multiple deflections. Other materials may be suitable in selected applications such as the present application in which the material is bent once and held in a fixed position. In other applications, the deflectable resistor may be used to measure inelastic deformation so that the substrate itself is inelastically deformable. Preferably, the substrate 15 should be deflectable without causing an electrical discontinuity or open circuit in the conductive material 16 while generally maintaining its electrical insulating characteristics. Of course, in the substrate 15 of the present embodiment does NOT move but is rigidly held in place and in a deflected condition. Thus the substrate 15 may be any suitable insulating material that can be suitably deployed in a matter such as that seen in FIG. 3

The conductive material or variable resistance material 16, also referred to herein as a conductor means, may be a two-part epoxy material, a thermoset adhesive, or a thermoplastic, all incorporating conductive material such as graphite or carbon. The variable resistance material may include a carbon ruthenium. To attach to a substrate, the conductive material 16 may include a material which facilitates wetting, gluing, or sticking. The conductive material 16 may include graphite in combination with a binder. The conductive material 16 is preferably of the type which is applied to the substrate in liquid form and which in turn dries to a solid form. The conductive material 16 may be spray painted, rolled, silk screened, or otherwise printed onto the substrate 15. The variable resistance material may also be a solid which is pressed onto the substrate 15. In some applications, a conductive substrate may be used. For other applications, the substrate may be connected to a particular potential, such as ground.

As an examples, the substrate 15 may be from about 0.003 to about 0.007 inches in thickness (although various other thicknesses may be acceptable); and the conductive material 16 may be from about 0.0006 to about 0.0011 inches in thickness although various other thicknesses may be acceptable so long as the substrate 15 can be deflected or bent as desired.

Humidity sensitive sensor 10 may be used to measure a change in the level of humidity or relative moisture content with respect to a starting or static moisture content or condition. The humidity sensitive sensor 10 is adapted to measure changes in a humidity factor ranging from 0% to 100%.

Figure 2:
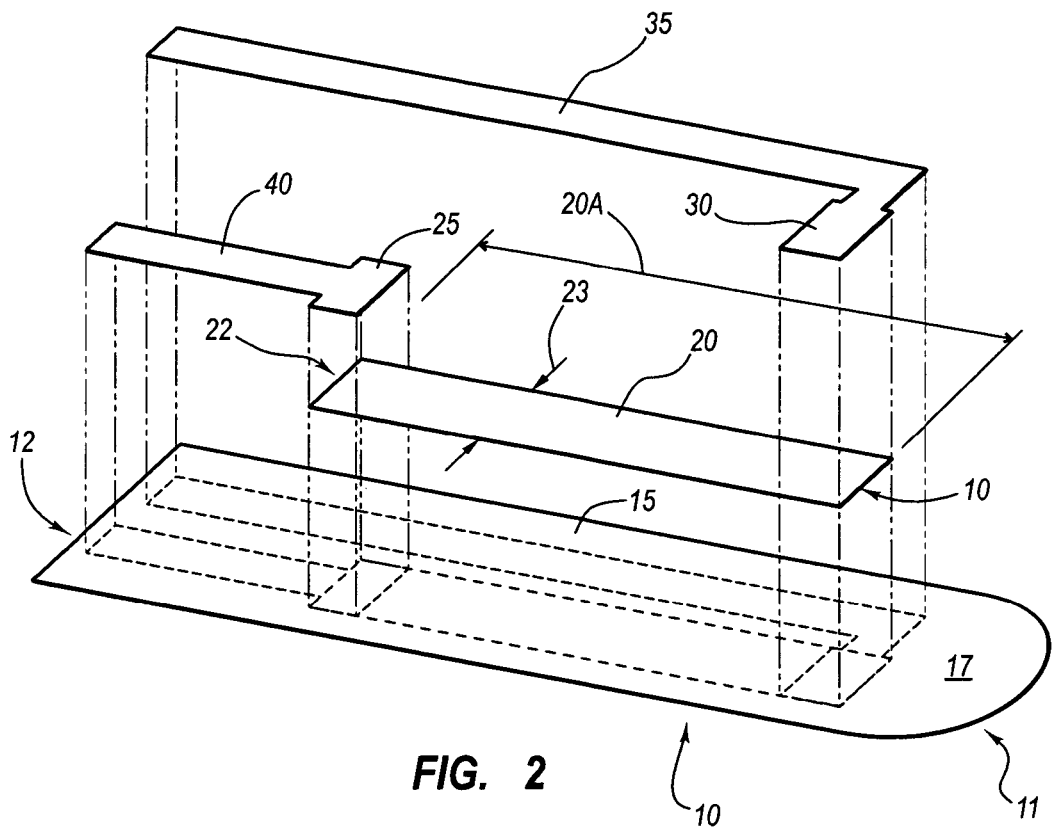
FIG. 2 illustrates an exploded view the substrate, the first layer of conductive material, the first conductor and the second conductor.

FIG. 2 illustrates an exploded view the humidity sensitive sensor 10 in accordance with one aspect of the present invention. In the illustrated embodiment, the top of humidity sensitive sensor 10 comprises a first top layer of electrically conductive ink 20 disposed on the top surface 17 of substrate 15. The first layer of electrically conductive ink 20 has a first end 21, a second end 22, a length 20A extending from the first end 21 to the second end 22 and a width 23. The first end 21 of the layer of electrically conductive ink 20 is proximate the first end 11 of substrate 15. The second end 22 of the conductive ink layer 20 is proximate the second end 12 of substrate 15. In the illustrated embodiment, the length 20A and width 23 of the electrically conductive ink layer 20 are both less than the length 13A and the width 13B of substrate 15.

It should be appreciated that the while the embodiment illustrated in FIGS. 1 and 2 depicts a substrate 15 with a layer of conductive material 16 on the top surface 15A, any number of shapes, sizes and lengths may be used. For example, humidity sensitive sensor 10 may comprise multiple legs each having a substrate with multiple layers of conductive material disposed on the top and/or bottom surface of the substrate like substrate 15. In this manner, humidity sensitive sensor 10 may have two or more lengths like length 13A, each having a layer of conductive material disposed thereon, with each of the layers of conductive material joined together by a run of conductive material.

As illustrated in FIG. 2, the first layer of conductive material 20 that is disposed on the top surface 17 is illustrated as suspended above the substrate 15. The first end segment 25 having a first conductive metal run 40 (i.e., a first conductor) and the second end segment 30 having a second conductive metal run 35 (i.e., a second conductor) are also shown suspended above the layer of conductive material 20. In operation, the resistance of conductive material 20 is measured between first conductor 25 and second conductor 30 by applying an electrical signal (voltage or current) to the first conductive metal run 40 and the second conductive metal run 35. Accordingly, first conductive metal run 40 and second conductive metal run 35 terminate near the second end 12 to facilitate connection to a suitable supply.

Figure 3:
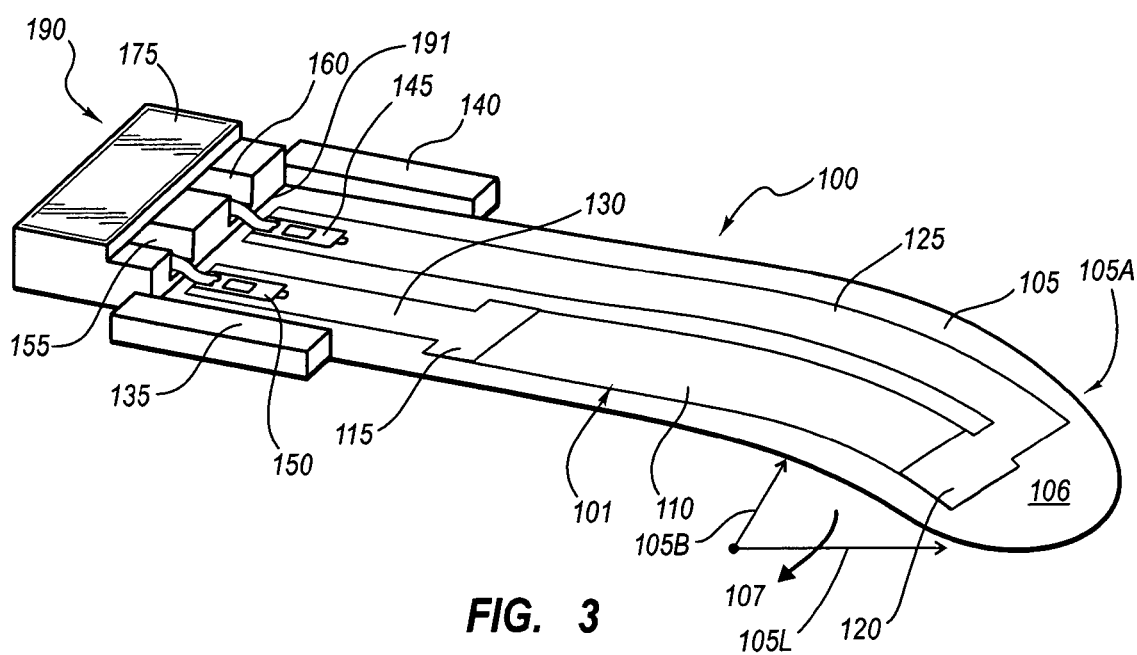
FIG. 3 illustrates a top perspective view of a humidity sensitive sensor manufactured with a permanent bend in the substrate to facilitate sensing variations in a humid environment.

Referring now to FIG. 3, a humidity sensitive sensor 100 is shown having a substrate 105 in a static position. In a humid environment, the static position for humidity sensor 100 is preferably defined by a curve or bend 105A in the substrate 105 where the curve or bend 105A is defined by a first radius 105B and possibly a second radius 105C which may be equal to or different in magnitude from first radius 105B. The curve 105A may also be defined by multiple other radii and radii having a center or origin that all differ. In general there is only one radius to which the sensor is fixed. The intent is to open the micro cracks sufficiently to allow the migration of moisture into the sensor matrix. It has been discovered that providing a substantially flat substrate 15 does not provide the preferred operating characteristics. That is, a humidity sensor could be flat, but it is optimum and thus preferred to provide a substrate 105 with a permanent bend or curve, as shown curve 105A in both FIGS. 3 and 5, added during the manufacturing process or when the sensor 100 is installed in use.

Substrate 105 has a first top layer of conductive material 101 disposed on the top surface 106 of substrate 105. In the illustrated embodiment, the conductive material 101 comprises a first conductor 115 electrically coupled to one end of a layer of conductive ink 110 and a second conductor 120 electrically coupled to a second end of the layer of conductive ink 110. First conductor 115 is coupled to a first conductor run 130 and second conductor 120 is coupled to second conductor run 125. The first and second conductor runs 125, 130 terminate at the edge of substrate 105 to facilitate connecting to a connector 190.

It has also been found that, for measuring the moisture content in an environment having a variable level of humidity, the change of resistance occurs when the conductive ink 110 is exposed to the environment. As discussed hereinafter, the first conductor run 120 and the second conductor run 125 are connected to an external circuit to transmit a voltage or current across or through the conductive ink with changes of resistance being measurable based on corresponding changes in either the current or the voltage using the classic Kirchoff formula of $$E = RI$$

Where E equals voltage in volts.

R equals resistance in ohms.

I equals current in amperes

Figure 4:
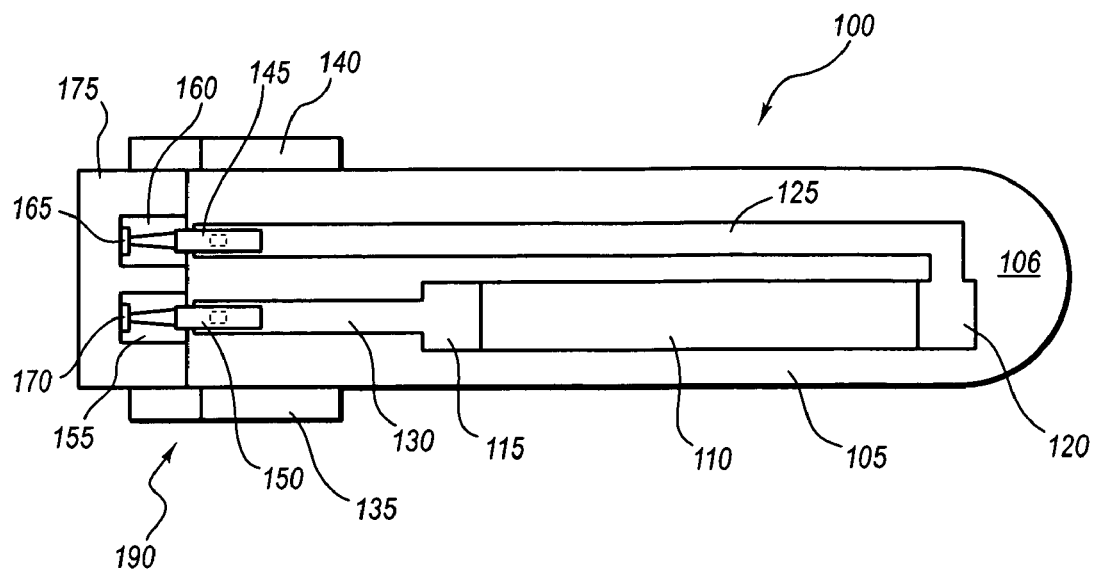
FIG. 4 illustrates a top view of the humidity sensitive resistor of FIG. 3.
Figure 5:
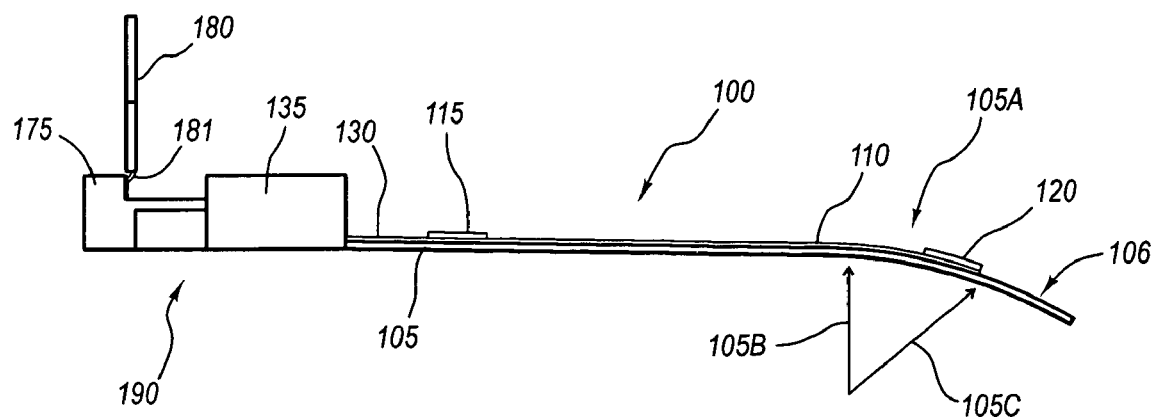
FIG. 5 is a side view of the humidity sensitive resistor of FIG. 3.

FIGS. 3, 4 and 5 together illustrate one embodiment of a connector 190 adhered to the bottom 191 of substrate 110 and electrically coupled to conductor runs 125, 130. Connector 190 is but one of many possibilities, and is illustrated and described to show one method for connecting to an external circuit for measuring resistance from and applying a measuring signal (e.g., voltage/current) to the sensor 100. Accordingly, the description of connector 190 provided herein is in no way intended to limit the use of other suitable connectors and should not be interpreted as such.

Connector 190 is adapted to provide an electrical signal to conductor runs 125, 130 and hence, first conductor 115 and second conductor 120, so as to measure the resistance of the conductive ink 110. Connector 190 comprises a left connector wall 135 and right connector wall 140. The width of substrate 105 matches the distance from left wall 135 to right wall 140, thereby creating a relatively tight fit when sliding the humidity sensor substrate 105 into the connector 190.

The substrate 105 rests against or in close proximity to the face of the connector housing 175 so as to bring first conductive run 125 and second conductor run 130 in close proximity to left connector channel 155 and right connector channel 160. In this way, the left electrical connector means 150 may be electrically coupled to the second conductor run 130 and the right electrical connector means 145 may be electrically coupled to the first conductor run 125. Right electrical connector means 145 extends into right connector channel 160 and electrically couples to right housing connector 165. Similarly, left electrical connector means 150 extends into left connector channel 155 and electrically couples to left housing connector 170. Left housing connector 170 and right housing connector 165 are electrically coupled to a pin receiving means (not shown) that is adapted for providing an electrical signal to the humidity sensor 100.

FIG. 5 illustrates a cover 180 and hinge 181 (not shown in FIGS. 3 and 4), adapted to fold between connector walls 135, 140. In so doing, cover 180 protects connector components comprising the housing connectors 165, 170, connector channels 155, 160 and electrical connectors 145 and 150. In operation, cover 180 is coupled to connector housing 175 by a thin piece of plastic material 181 that operates as a hinge. Cover 180 folds down towards the substrate 105 and between connector sides 135, 140, and snaps into place in grooves (not shown) in connector sides 135, 140 so as to form a tight fit and thereby a protective covering for the connector components.

In operation, when substrate 105 is exposed to moisture in the static configuration illustrated in FIGS. 3 and 5, the resistance of the first top layer of conductive material 101 predictably changes. The measurement of the change of resistance of the first top layer of conductive material 101 from the static configuration (i.e. a first condition having a first moisture content on the surface of substrate 105 defined to be the starting or static condition) to a condition with an elevated moisture content (i.e. a second condition having a second moisture content on the surface of substrate 105) reflects the change in moisture content or change in humidity. While the present embodiment deals is principally intended to measure water vapor and in turn the amount of water vapor in air or humidity, it may also be used to measure other vapors in other gases.

Stated another way, the resistance of the sensor conductive ink 110 and the resistance of the moisture on the surface of the conductive ink 110 are two variables represented by the following equation:

$$1/R_{total} = 1/R_{moisture} + 1/R_{conductive\ ink}$$

Since the sensor 100 is in a fixed bent configuration, the resistance of the conductive ink layer 110, $R_{conductive\ ink}$, is fixed and measurable. As the moisture content on the conductive ink changes, the resistance of the moisture content, $R_{moisture}$, changes as well.

As the moisture level approaches 0%, the resistance of the moisture approaches infinity, and therefore the portion attributable to the moisture content, $1/R_{moisture}$, approaches zero. Accordingly, the resistance of the conductive ink layer 110 becomes visible and since $R_{conductive\ ink}$ is fixed and measurable, $1/R_{total}$ is almost completely attributable to the resistance of the conductive ink layer 110. With measurements, a relationship between the resistance of the conductive ink layer 110 at a static condition, $R_{conductive\ ink}$, and the total resistance, $R_{total}$, of the conductive ink layer 110 exposed to humidity or moisture having a resistance $R_{moisture}$ can be developed and used in software or hardware, that is relatively simple to create.

Continuing with the operation of humidity sensitive sensor 100, micro-cracks (not shown) are added to the variable resistance material 101 during the manufacturing process. It is believed that as a sensor 100 (of some or all compositions) is bent, the distance between the micro-cracks of the variable resistance material 101 separates or widens. That is, in some or all compositions, dried variable resistance material has micro-cracks in a granular or crystalline-type structure which widens and separates upon deflection.

As the variable resistance material 101 bends, the space between the cracks is believed to increase, thereby changing the electrical resistance in a predictable manner. With the humidity sensor 100 in a bent configuration, molecules of the liquid (e.g., water) vapor in the gas migrate into the cracks and in turn induce a change in electrical resistance which can then be measured upon application of suitable electrical signals. The change in resistance between the first configuration illustrated (static configuration) and a second configuration having a moisture content on or at the surface of the sensor 100 (not shown) can be measured upon the application of suitable electrical signals to first conductor run 125 and second conductor run 130.

Figure 6:
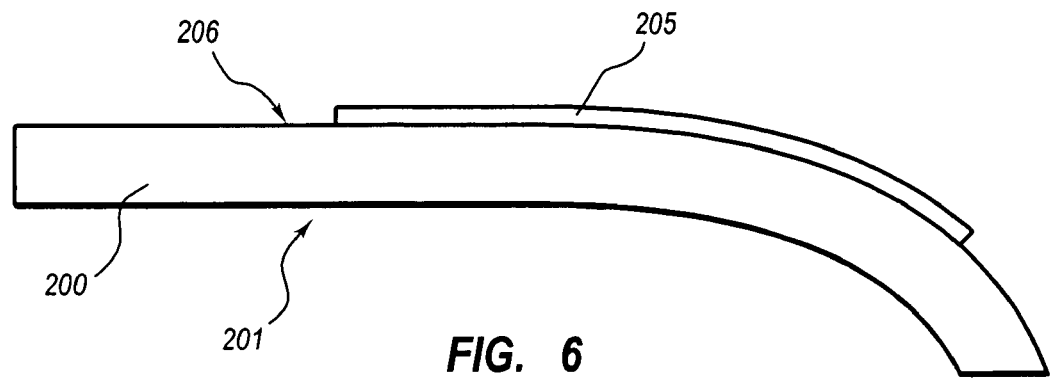
FIG. 6 is a substantially enlarged cross-section view of a portion of a humidity sensitive resistor in a static position.

The sensor 201 of FIG. 6 is shown in side view and substantially enlarged view. Conductor means 205 is adhered to the top surface 206 of substrate 200. As shown in the left side view of FIG. 7, the sensor 201 includes a first conductor 210 and a second conductor 215 adhered to the surface of conductor means 205. The first conductor 210 has a first conductive run 211 that extends along the surface 206 of substrate 200. As shown in the right side view of FIG. 8, second conductor 215 has a second conductor run 216 that also extends along the top surface 206 of substrate 200.

The first conductor 210, second conductor 215 and first and second conductor runs 211, 216 (e.g., layers of electrically conductive material) are formed of an electrically conductive material. In one arrangement, the first conductor 210 and second conductor 215 have been successfully formed of silver. It is also believed formable from conductive silver alloys, and other conductive metals, as well as carbon-based compounds. In a preferred arrangement, the first conductor 210 and second conductor 215 are adhered to the conductive ink and, in turn, have a thickness which is from about 0.01 millimeters to about 0.02 millimeters and preferably about 0.015 millimeters.

The first conductor 210, second conductor 215 and first and second conductor runs 211, 216 retain their electrical conductivity upon deflection. With the first conductor 210 and second conductor 215 affixed or adhered to the conductor means 205, the resistance may still vary somewhat over time, but the degree of variance is either within acceptable tolerances or otherwise measurable from time to time so that adjustments can be made to accommodate for the drift in resistance over time.

Figure 7:
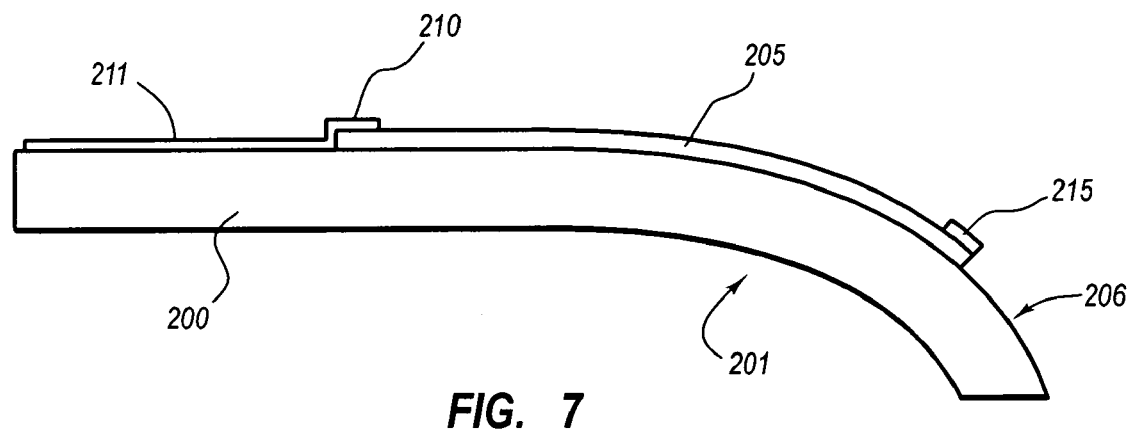
FIG. 7 is a substantially enlarged cross-section, right side view of a portion of a portion of a humidity sensitive resistor showing the conductive material and the first and second conductors.
Figure 8:
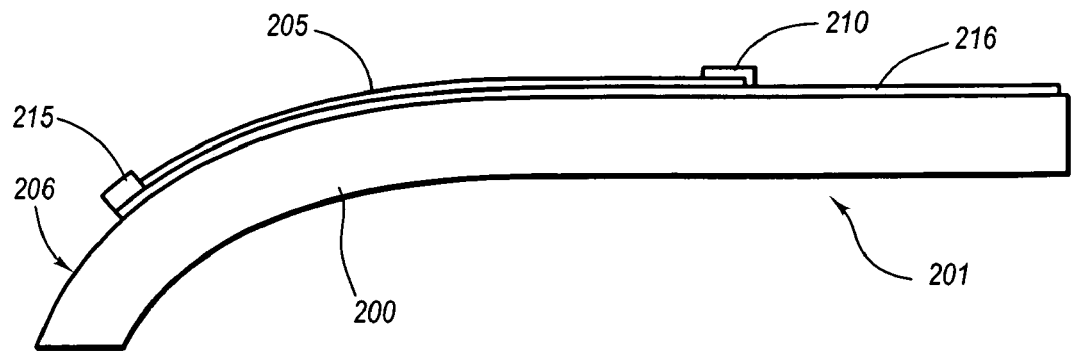
FIG. 8 is a substantially enlarged cross-section, left side view of a humidity sensitive resistor showing the conductive material and the first and second conductors.

Referring to FIGS. 6, 7 and 8, the substrate 200 is shown to have a thickness which is here shown substantially disproportionate to the true thickness of the substrate, solely to facilitate illustration. That is, for the substrate 200 to be elastically deflectable, it is preferred that its thickness be from about 0.07 to about 0.25 millimeters. If it is to be inelastically deflectable, the material and thickness must be appropriately selected.

The conductor means 205 of FIGS. 6, 7 and 8 is typically a conductive ink which is adhered to the top surface 206 of the substrate 200. By adhere, it is meant that the conductive ink is attached to the substrate, because the conductive ink includes a material which facilitates wetting, gluing, or sticking. A conductive ink suitable for the illustrated embodiment is available from Flexpoint Sensor Systems, 106 West 12200 South, Draper, Utah 84020 and identified as part number 365 or DOH 10 or variations thereof. The selected ink includes graphite in combination with a binder.

As illustrated in FIGS. 6, 7 and 8, the conductive ink 205 is deposited to adhere to the surface 206 of the substrate 200 and, in turn, has a thickness which is here illustrated substantially larger than the actual thickness. That is, the thickness of the layer of conductive ink 205 is illustrated disproportionate to the actual thickness of the substrate 200 and of the actual layer of the conductive ink 205. In the preferred embodiment, the thickness of the conductive ink 205 is from about 0.01 millimeters to 0.02 millimeter and desirably about 0.015 millimeters.

In typical sensor applications, a top layer of protective coating is added that protects the conductive ink 205, first and second conductors 210, 215 and first and second conductor runs 211, 216 from damage. As a humidity sensor, it has been found that such a protective coating inhibits the operation of the humidity sensor. Therefore, in the preferred embodiment, a final layer containing the top protective coating is not added to humidity sensitive sensor 201. Therefore, conductive ink 205, first and second conductors 210, 215 and first and second conductor runs 211, 216 are exposed to the atmosphere. In an alternative embodiment, the conductive ink 205 is exposed to the atmosphere and everything else, including first and second conductors 210, 215 and first and second conductor runs 211, 216 is protected by a top layer of protective coating.

Figure 9:
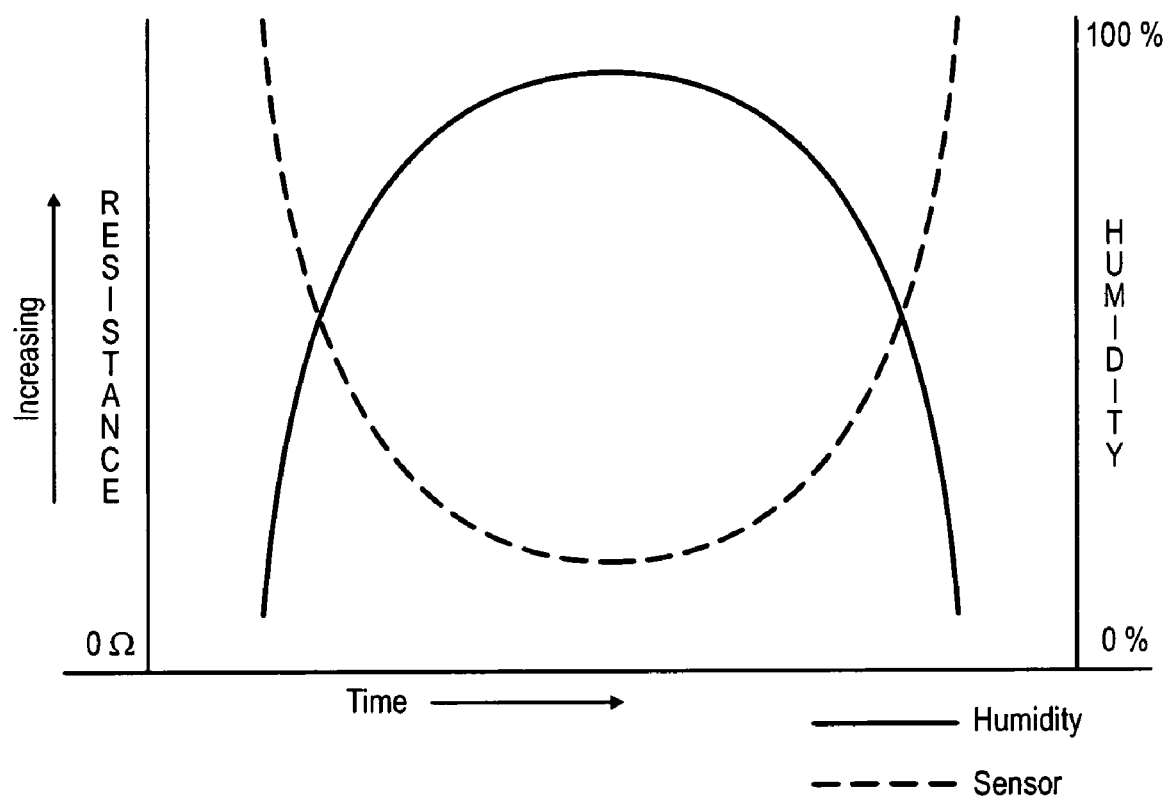
FIG. 9 shows a graph illustrating the correlation between resistance and humidity over time on the top surface of deflectable resistor.

FIG. 9 shows a graph illustrating the correlation between resistance and moisture or humidity level. The x-axis of the graph is labeled time and the two y-axis are labeled humidity and resistance of the bend sensor material. In the illustrated graph for a typical example, as time increases along the x-axis, the amount of humidity that comes in contact with the bend sensor material 110 increases as well. As shown, the resistance of the bend sensor material decreases as the amount of moisture content increases. Accordingly, the resistance of the bend sensor material 110 changes in a measurable manner with respect to the moisture content and can be determined using a simple computer program or the like. Therefore, since there is a substantial one-to-one correlation between moisture content and resistance, a measurement of the moisture content in the atmosphere may be determined from the change in resistance of the material 110.

Figure 10:
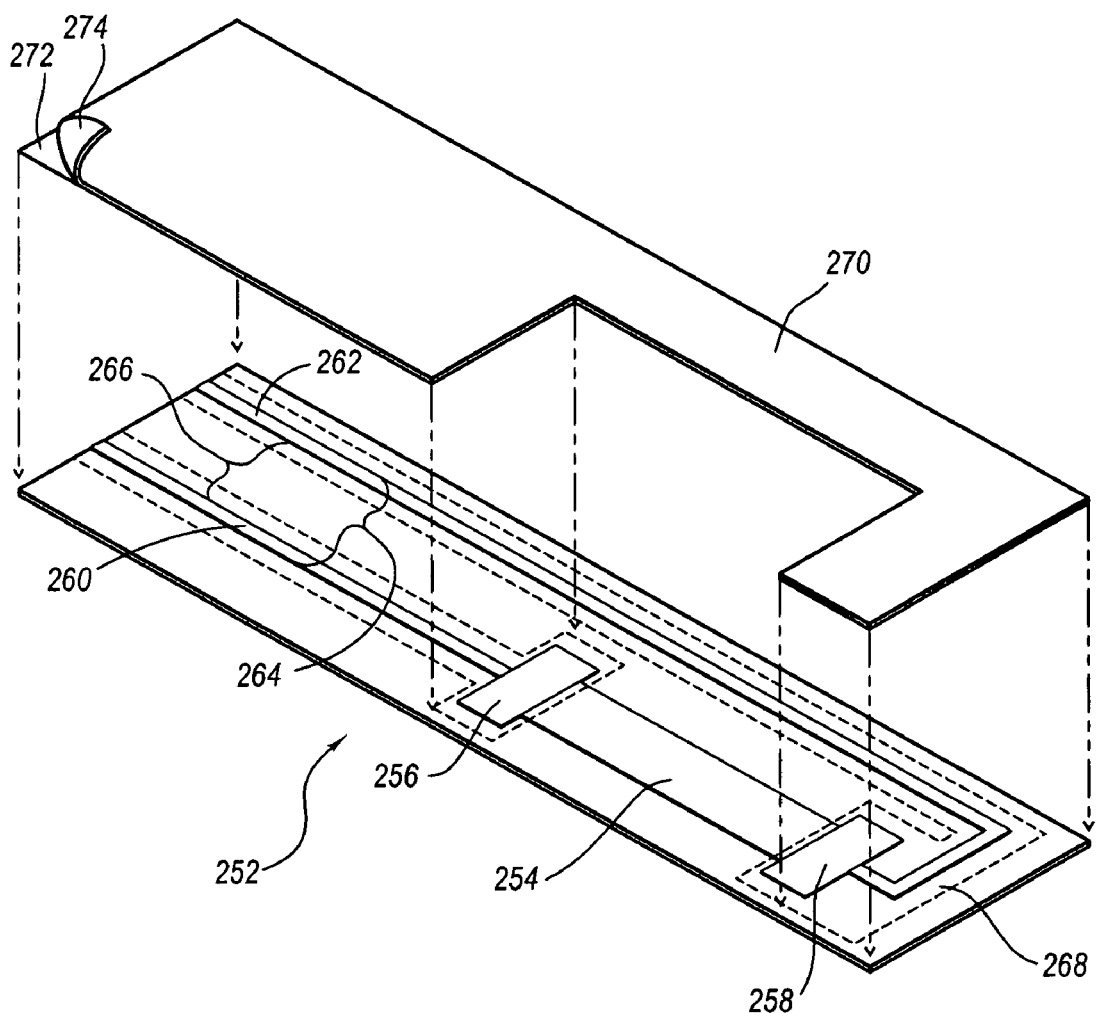
FIG. 10 is an exploded perspective showing anti-migration material and a fourth layer exploded away from the substrate.

Turning to FIG. 10, a flexible potentiometer 250 includes a substrate 252 with a conductive ink 254 connected by connecting sections 256 and 258 to conductors 260 and 262 in a manner much the same as described in FIGS. 1-8. The conductors 260 and 262 have been observed to migrate. That is, molecules of the material of the conductors 260 and 262 migrate from one conductor toward another to form branches 264 and limbs 266 under the influence of the electrical current passing through and high humidity environments. The branches 264 and limbs 266 can eventually reach another portion of the conductors 260 and 262 and eventually lead to a short between conductors 260 and 262. To reduce the migration and in turn the generation of branches 264 and limbs 266, a protective coating 268 shown by dotted lines is deposited over the top of the conductors 260 and 262 as well as connecting sections 256 and 258. It is not deposited on top of the conductive ink 254. Any suitable coating that prevents the migration will be sufficient. In practice, a carbon material MINICO (301P1H) made by Acheson Colloids Company, a division of National Starch, of Ontario, Calif. has been found to be suitable.

In addition to the protective coating 268, or separately, a moisture barrier 270 may be deposited over the entire substrate 252 or selected portions with the exception of the conductive ink 254. The moisture barrier 270 is preferably a curable ink or dielectric that is about 0.5 mil thick. It may be made of first coat 272 which is deposited by spraying or other suitable process for depositing a thin film on a substrate. The first coat 272 is dried or cured using suitable heat or a UV signal. Thereafter, a second coat 274 is added which is comparable to the first coat 272. The second coat 274 is also cured using ultra violet radiation. While other thin barrier coats may be used, it has been found that ELECTRODAG UV 1015 (26NCP68) also offered by Acheson Colloids Company is suitable. The moisture barrier 270 restricts migration of moisture or other fluid vapor from the gas or atmosphere into, onto and under the conductors 260 and 262. In turn, the resistance of the conductors 260 and 262 is not impaired or impacted to in turn impair the function of the humidity detector over time.

Figure 11:
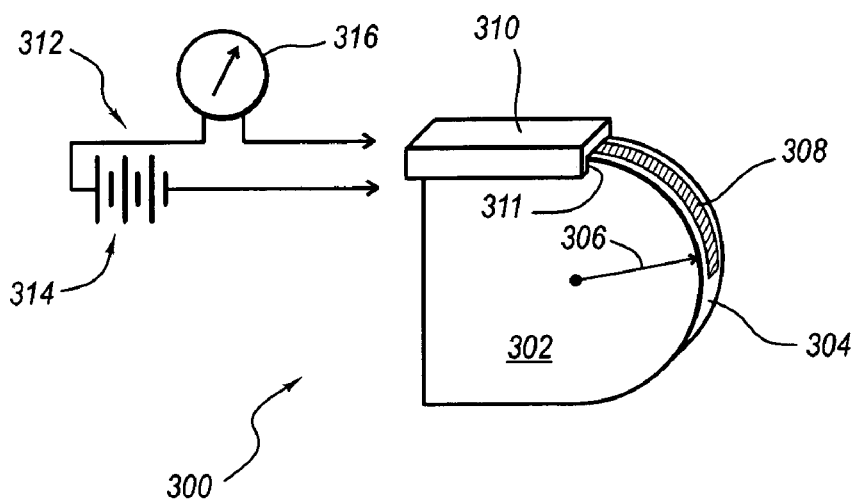
FIG. 11 is a side and exploded view of a humidity sensor of the present invention.

Turning to FIG. 11, an actual humidity sensor 300 is depicted but enlarged for ease of illustration. The sensor 300 includes a base 302 made from any suitable insulating solid plastic and formed with a round face 304 having a single fixed radius 306. In the device illustrated in FIG. 11, the radius 306 is about 3/16 of an inch. Of course humidity sensors can be made with a radius 306 that varies from about 1/8 of an inch upward to desired any size (e.g., 2-3 inches). A suitable flexible potentiometer 308 is attached to the face 304 and connected to a connector 310 positioned in a notch 311 for further connection to an external circuit 312 having a battery 314 or other suitable source of electrical power and an ammeter 316 to show the electrical current flowing in the circuit 312 when the circuit 312 is connected to the connector 310 and in turn to the flexible potentiometer 308. Thus as the humidity changes, the electrical resistance of the flexible potentiometer 308 varies in turn varying the electrical current which can be displayed by the ammeter 316 or any other suitable display device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A humidity sensitive resistor comprising:
   a substrate having a first surface and a second surface spaced from said first surface, said substrate having a permanent bend portion that is arcuate;
   a resistive element disposed on at least said permanent bend portion, said resistive element having a first end and a second end, said resistive element including a conductive material and a material for affixing said resistive element to said substrate, said resistive element being exposed to an atmosphere having a static condition moisture content, said resistive element having an electrical resistance that changes predictably when said moisture content of said atmosphere in contact with said resistive element changes from said static condition;
   a first conductor electrically connected to said first end of said resistive element; and
   a second conductor electrically connected to said second end of said first resistive element.

2. The humidity sensitive resistor of claim 1 further comprising:
   a first connector means coupled to said first conductor for interconnection to external electrical components; and
   a second connector means coupled to said second conductor for interconnection to external electrical components.

3. The humidity sensitive resistor of claim 1 wherein said first conductor is coated with anti migration material to inhibit the migration of material of said first conductor to and between said first conductor and said second conductor.

4. The humidity sensitive resistor of claim 3 wherein said second conductor is coated with anti migration material to inhibit the migration of material of said second conductor to and between second conductor and said first conductor.

5. The humidity sensitive resistor of claim 3 wherein said first conductor and said second conductor are made of a precious metal.

6. The humidity sensitive resistor of claim 5 wherein said precious metal is silver.

7. The humidity sensitive resistor of claim 3 wherein said anti migration material is carbon.

8. The humidity sensitive resistor of claim 1 further comprising a sealing layer positioned over said first conductor and said second conductor and not said resistive element, said sealing layer being a material to inhibit the movement of moisture there through.

9. The humidity sensitive resistor of claim 8 wherein said sealing layer is a dielectric.

10. The humidity sensitive resistor of claim 8 wherein said sealing layer is an ink which is curable by ultraviolet rays.

11. The humidity sensitive resistor of claim 10 wherein said sealing layer is comprised of a first coat of said ink which is cured by ultraviolet rays and a second coat of ink placed over said first coat of ink which second coat is cured by ultraviolet rays.

12. The humidity sensitive resistor of claim 11 wherein said first coat and said second coat together have a thickness from about 0.3 mil to about 0.8 mil.

13. The humidity sensitive resistor of claim 1 wherein first conductor is coated with anti migration material, wherein said second conductor is coated with said anti migration material, and said resistive element is not coated with anti migration material, said anti migration material being of the type to inhibit the migration of material of said first conductor and between said second conductor.

14. The humidity sensitive resistor of claim 13 further comprising:
   a sealing layer positioned over said first conductor and said anti migration layer and said second conductor and said anti migration layer, said sealing layer being made of a material to inhibit the movement of moisture there though.

15. A humidity sensitive resistor comprising:
   a substrate having a permanent bend portion that is arcuate;
   a resistive element disposed on at least said permanent bend portion, said resistive element having a first end and a second end, said resistive element including a conductive material and a material for affixing the said resistive element to said substrate, said resistive element being exposed to an atmosphere at a first humidity, said resistive element having an electrical resistance that changes predictably when said humidity of said atmosphere changes from said first humidity to a second humidity;
   a first conductor electrically connected to said end of said first resistive element; and
   a second conductor electrically connected to said second end of said resistive element.

16. The humidity sensitive resistor of claim 15 wherein said substrate has a surface and wherein said resistive element, said first conductor and said second conductor are located on said surface of said substrate.

17. The humidity sensitive resistor of claim 16 wherein said bend portion is configured to have at least one radius.

18. The humidity sensitive resistor of claim 16 further comprising a base which has an arcuate surface and wherein said substrate is affixed to said arcuate surface of said base to form said arcuate portion.

19. The humidity sensitive resistor of claim 18 wherein said change of electrical resistance of said resistive element corresponds to a predetermined change in the relative humidity of said atmosphere.

20. The humidity sensitive resistor of claim 15 wherein said resistive element is a conductive ink.

21. The humidity sensitive resistor of claim 20 wherein said first conductor and said second conductor are made of a soft conductive metal.

22. The humidity sensitive resistor of claim 21, wherein said soft conductive metal is a silver or a silver alloy.

23. A humidity sensitive resistor comprising:
   a substrate having a first surface and a second surface spaced from and opposite to said first surface, said substrate having a permanent bend portion that is arcuate;
   a resistive element having electrical resistance and disposed on said substrate in a desired configuration, said resistive element having a first end and a second end, said resistive element being exposed to the atmosphere having a first humidity changeable to a second humidity, said resistive element having a first resistance in said atmosphere corresponding to said first humidity and a second resistance in said atmosphere corresponding to said second humidity, the difference between said first resistance and said second resistance representing the change between said first humidity and said second humidity.

24. The humidity sensitive resistor of claim 23, further comprising:
   a first conductor electrically connected to said first end of said resistive element; and a second conductor electrically connected to said second end of said resistive element.

25. The humidity sensitive resistor of claim 24 wherein said first conductor and said second conductor are made of a soft conductive metal.

26. The humidity sensitive resistor of claim 25 wherein said soft conductive metal is silver or a silver alloy.

27. The humidity sensitive resistor of claim 25 wherein said soft conductive metal is carbon or a carbon compound.

28. The humidity sensitive resistor of claim 24 further comprising:
   a first connector means coupled to said said first conductor for interconnection to external electrical components; and
   a second connector means coupled to said second conductor for interconnection to external electrical components.

29. A humidity sensor comprising:
   a substrate having a width and a length, said substrate being formed with a permanent bend along said length;
   a first electrical conductor disposed on said substrate, said first electrical conductor having a first end and a second end opposite said first end with a length therein between oriented in general alignment to the length of said substrate, said first electrical conductor being exposed to a gas having a variable humidity and being formed of electrically conductive material having an electrical resistance that changes predictably with the change of the humidity of said gas;
   a second layer of electrically conductive material electrically connected to a first end of said first layer of conductive material; and
   a third layer of electrically conductive material electrically connected to a second end of said first layer of conductive material.

30. A method for varying the resistance in an electrical circuit exposed to a humid environment, said method comprising:
   providing a substrate having a first surface and a second surface spaced from and opposite to said first surface, said substrate having a deflected portion that is rigidly deflected;
   positioning a resistive element on said rigidly deflected portion of said substrate in a desired configuration, said resistive element having a first end and a second end;
   positioning said resistive element in an atmosphere that changes between a first humidity and a second humidity, the electrical resistance of said resistive element changing predictably as said atmosphere changes between said first humidity and second humidity;
   positioning a first conductor on said substrate and connecting said first conductor to said first end of said resistive element;
   positioning a second conductor on said substrate and connecting said second conductor to said second end of said resistive element; and
   attaching connector means to each of said first conductor and second conductor each for connection to external electrical components.

31. The method of claim 30 further comprising:
   applying anti migration material to and between said first conductor and said second conductor excluding said resistive element to inhibit the migration of material to and between said first conductor and said second conductor when electrical current is passing thereto.

* * * * *